(12) United States Patent
Ladocsi et al.

(10) Patent No.: US 7,330,818 B1
(45) Date of Patent: Feb. 12, 2008

(54) HEALTH AND LIFE EXPECTANCY MANAGEMENT SYSTEM

(75) Inventors: Lewis T. Ladocsi, Short Hills, NJ (US); Richard C. Miller, Chatham, NJ (US)

(73) Assignee: Lifespan Interactive: Medical Information Management. LLC., Short Hills, NJ (US)

( * ) Notice: Subject to any disclaimer, the term of this patent is extended or adjusted under 35 U.S.C. 154(b) by 249 days.

(21) Appl. No.: 09/709,233

(22) Filed: Nov. 9, 2000

(51) Int. Cl.
*G06Q 10/00* (2006.01)

(52) U.S. Cl. .................... 705/3; 705/2; 705/4; 600/300; 600/301

(58) Field of Classification Search ............... 705/2–4; 600/300–301; 128/630
See application file for complete search history.

(56) References Cited

U.S. PATENT DOCUMENTS

| | | | |
|---|---|---|---|
| 4,609,812 A | 9/1986 | Drexler | 235/487 |
| 4,621,729 A | 11/1986 | Jackson | 206/37 |
| 4,632,428 A | 12/1986 | Brown | 283/76 |
| 4,680,459 A | 7/1987 | Drexler | 235/487 |
| 4,692,394 A | 9/1987 | Drexler | 430/140 |
| 4,745,268 A | 5/1988 | Drexler | 235/487 |
| 4,818,852 A | 4/1989 | Haddock et al. | 235/488 |
| 4,835,376 A | 5/1989 | Drexler | 235/488 |
| 4,868,376 A | 9/1989 | Lessin et al. | 235/492 |
| 5,031,161 A * | 7/1991 | Kendrick | 368/29 |
| 5,193,855 A * | 3/1993 | Shamos | 283/117 |
| 5,291,399 A | 3/1994 | Chaco | 705/3 |
| 5,301,105 A | 4/1994 | Cummings, Jr. | 705/2 |
| 5,499,293 A | 3/1996 | Behram et al. | 705/76 |
| 5,509,083 A | 4/1996 | Abtahi et al. | 382/124 |
| 5,590,038 A | 12/1996 | Pitroda | 705/41 |
| 5,596,652 A | 1/1997 | Piatek et al. | 382/115 |
| 5,597,182 A | 1/1997 | Reber et al. | 283/67 |
| 5,659,741 A | 8/1997 | Eberhardt | 707/104.1 |
| 5,682,027 A | 10/1997 | Bertina et al. | 235/380 |
| 5,692,501 A * | 12/1997 | Minturn | 128/630 |
| 5,763,862 A | 6/1998 | Jachimowicz et al. | 235/380 |
| 5,793,882 A | 8/1998 | Piatek et al. | 382/115 |
| 5,823,948 A | 10/1998 | Ross, Jr. et al. | 600/300 |
| 5,832,488 A | 11/1998 | Eberhardt | 707/10 |

(Continued)

OTHER PUBLICATIONS

Kapellas, Michael, "Measuring mortality Put your lifestyle on the line with a visit to an Internet site that lets you test your life expectancy", Journal Star, Peoria, Feb. 2, 1999, p. C 10.*

(Continued)

*Primary Examiner*—C. Luke Gilligan
*Assistant Examiner*—Vivek Koppikar
(74) *Attorney, Agent, or Firm*—Ohlandt, Greeley, Ruggiero & Perle, L.L.P.

(57) ABSTRACT

A life expectancy management system which comprises: a storage means which is capable of storing data, such as genetic data, birth data, lifestyle data, pediatric health data, and adulthood health data; a means for altering the data based upon the occurrence of at least one event selected from the group consisting of: chronic and routine health events, emergency health events, pregnancy data and medical advancements; and a prediction modeling logic which provides a predetermined life expectancy that can be reduced by deviations from expectations which are calculated from the data and altered or adjusted data. Optionally, a means for providing recommended goals based upon the life expectancy predicted and the predetermined life expectancy.

22 Claims, 4 Drawing Sheets

U.S. PATENT DOCUMENTS

| | | | |
|---|---|---|---|
| 5,867,821 A * | 2/1999 | Ballantyne et al. | 705/2 |
| 5,877,742 A | 3/1999 | Klink | 345/123 |
| 5,884,271 A | 3/1999 | Pitroda | 705/1 |
| 5,899,998 A | 5/1999 | McGauley et al. | 707/104 |
| 5,915,242 A | 6/1999 | Tsujii | 705/3 |
| 5,937,387 A * | 8/1999 | Summerell et al. | 705/2 |
| 5,961,833 A | 10/1999 | Green et al. | 210/638 |
| 5,995,345 A | 11/1999 | Overbo | 360/133 |
| 5,995,965 A | 11/1999 | Experton | 707/10 |
| 6,011,858 A | 1/2000 | Stock et al. | 382/115 |
| 6,032,119 A | 2/2000 | Brown et al. | 705/2 |
| 6,042,005 A | 3/2000 | Basile et al. | 235/382 |
| 6,044,349 A | 3/2000 | Tolopka et al. | 705/1 |

OTHER PUBLICATIONS

Marchione, Marilynn, "Quiz a fun way to take a look at longevity", Milwaukee Jounal Sentinel, May 17, 1999, p. 1.*

Anonymous, "Live Long and Prosper into the Millenium with HealthCentral.com Featuring Dr. Dean Edell", Business Wire, Mar. 24, 1999, No. 39982983, 3 pages.*

"Quality control measures tracked for heart surgeons"; International Healthcare News, No. 14, p. 8, Jul. 1996, ISSN: 1359-9224. Dialog ID No. 01008665. (From Dialog File 9: Business & Industry ® ).*

* cited by examiner

HEALTH AND LIFE EXPECTANCY MANAGEMENT SYSTEM

The present invention pertains to a unique and novel life expectancy management system which continuously models an individual's potential life expectancy, potential IQ, probability of certain diseases and probability of accidental death based upon maternal and paternal genetic information, birth information, past and current health information, personal data, and advances in technology and medicine. In particular, the present invention allows for an individual to determine how certain lifestyle, nutritional, health and career changes can effect their potential life expectancy, so as to provide incentive to an individual to adjust such factors so as to increase the potential for a longer quality life expectancy.

BACKGROUND OF THE INVENTION

Presently, most healthcare patients, as well as their physicians, find it difficult to generate an accurate health profile since critical data is often missing. That is, the individual is typically unable to recall the exact nature of his/her illness, or dates, reasons or results of specific surgical procedures as well as pathology reports. There is also a lack of accurate information concerning medications taken by an individual as well as doses and dosage schedules which may result at times in life threatening drug interactions.

There have been various attempts at providing an individual with his or her personal medical history. One such computerized system for storing medical histories is disclosed in U.S. Pat. Nos. 5,659,741 and 5,832,488 (both to Eberhardt). These patents are directed to computer systems and methods for programming them for storage of individual medical histories on a storage device, preferably about the size of a credit card, for adding new medical data about the individual to the device and for communicating with other computers to retrieve large data records about the individual; and for enabling a second computer to collate and sort data relating to selected medical fields from the data of such individual and from the data about other individuals transferred to the second computer.

Neither of the aforementioned is capable of utilizing the stored data records other than for retrieval purposes by another computer. They provide no useful information to the individual in helping them to improve their life expectancy or overall wellness.

The present invention overcomes the aforementioned deficiencies of conventional smart cards which simply store health and personal data for later usage. That is, the present invention utilizes a novel modeling technique which is capable of taking basic medical/health information concerning an individual and formulating an optimal life-span (i.e., life expectancy) potential for that individual. This modeling technique can in itself be altered as influenced by evolutionary discoveries, e.g., new technologies developed in medicine or other areas which impact on overall life expectancy, change in an individuals overall health condition, and/or changes in an individuals lifestyle. This unique modeling technique can therefore be used as a tool for assisting an individual in how to conduct his or her lifestyle and/or as a guide for the healthcare provider in diagnosing or treating an individual, which heretofore has not been available.

Therefore, the present invention is capable of: (a) generating accurate health profiles from birth to death; (b) giving individuals the ability to be the primary guardian of his or her medical/health data; (c) providing the ability to continuously update an individual's medical/health data for the purpose of projecting life expectancy potentials and providing the ability to alter life expectancy potentials by lifestyle adjustments; (d) utilizing the medical/health database for goal oriented and incentive driven health management; (e) utilizing the medical/health database for community-based healthcare planning; and (f) optionally, selectively using the data for national healthcare planning, i.e., pertinent information for the Center for Disease Control and the Census Bureau.

The present invention also provides many additional advantages which shall become apparent as described below.

SUMMARY OF THE INVENTION

A life expectancy management system which comprises: a storage means which is capable of storing health profile data, such as genetic data, birth data, lifestyle data, pediatric health data, and adulthood health data; a means for altering or adjusting the data based upon the occurrence of at least one event selected from the group consisting of: chronic and routine health events, emergency health events, pregnancy data and medical advancements; and a prediction modeling logic which provides a predetermined life expectancy that can be reduced by deviations from expectations which are calculated from the health profile data and altered or adjusted data. Optionally, a means for providing recommended goals and incentives based upon the life expectancy predicted and the predetermined life expectancy.

The storage means is preferably a machine readable storage medium and the means for predicting life expectancy is a microprocessor comprising the prediction modeling logic. The means for altering or adjusting the original health profile data is a microprocessor and/or Internet service provider (ISP) which is in communication with the storage means.

The system optionally includes a means for providing secure access only to the health profile and altered/adjusted data, wherein secure access is selected from the group consisting of: fingerprint identification, footprint identification, DNA identification, imagery identification and password.

The present invention also includes a method for predicting the life expectancy of an individual, wherein the method comprising the following steps: establishing a predetermined life expectancy; storing health profile data; altering or adjusting the data based upon the occurrence of at least one event; and determining life expectancy by reducing the predetermined life expectancy based upon the data and/or the altered or adjusted data.

Other and further objects, advantages and features of the present invention will be understood by reference to the following specification in conjunction with the annexed drawings, wherein like parts have been given like numbers.

DESCRIPTION OF THE PREFERRED EMBODIMENTS

The present invention is directed to a health information database in a compact form that an individual possesses which contains all pertinent information relating to the individual's health and life expectancy. This database is dynamic, upgradable on a continuous basis and for use in an interactive fashion for an individual's health maintenance management. 'Interactive' relates to the interdependent relationship between the individual, the healthcare provider, and the vast amount of health related database.

Figure 1:
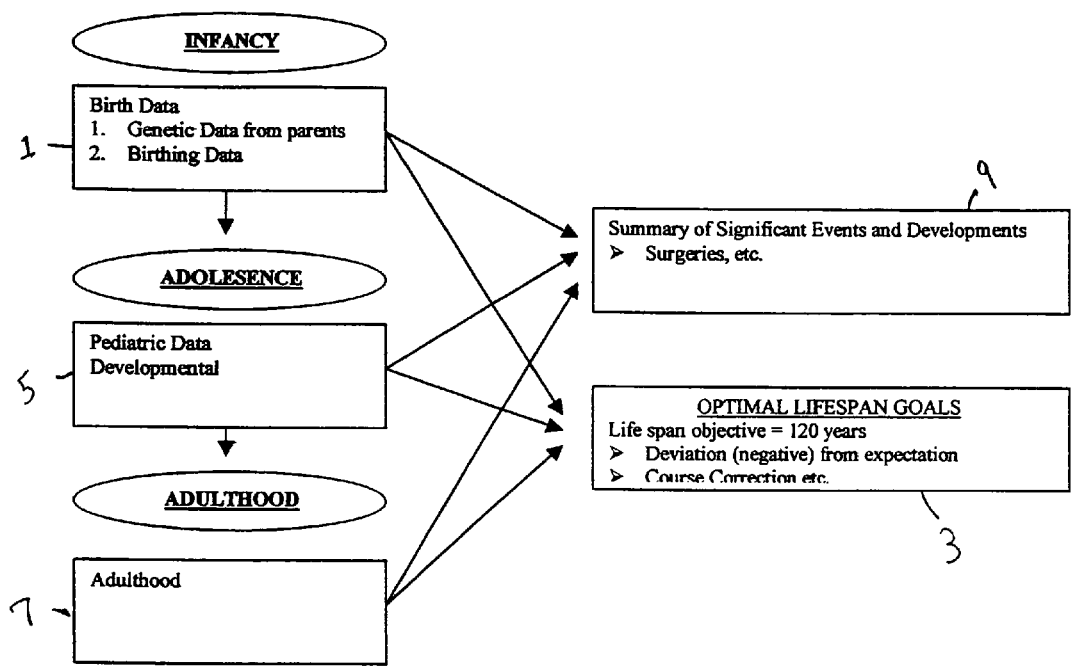
FIG. 1 is a schematic diagram of data used from infancy, adolescence and adulthood to establish optimal life expectancy goals.

Ideally, the health profile database will start with the birth data 1 as shown in FIG. 1. Birth data 1 can include genetic data from parents and birthing data. This will be the most accurate and most reliable basis for life expectancy projections 3. In most cases, however, careful collection of data will be required on a retrospective basis in order to generate the health profile data. Thus, the accuracy of such collected data will depend on the individual's ability to find original information.

The health profile data must be continuously updated throughout an individual's life in order to insure that the life expectancy projection is accurate. Therefore, the health profile data must be updated during infancy 1, adolescence 5 and adulthood 7. Adolescence data 5 may include all pediatric data, such as vaccinations, childhood diseases, allergies, vision, and overall child development. Adulthood data 7 may include health maintenance data generated from scheduled annual visit(s) to an individual's healthcare provider, e.g., general evaluation by primary healthcare provider, gynecological evaluations, appropriate laboratory data (blood tests, PAP smears and imaging data), annual dental evaluations, and specialty specific evaluations. Health maintenance data may also include occurrence visits to a healthcare provider for minor ailments needing attention or prescription medications and emergency visits which involve serious illness or misadventures (e.g., accidents).

Still other significant events and developments 9 such as surgical, medical or psychiatric therapy are also important in developing a life expectancy profile.

Life expectancy modeling normally starts with a life span or expectancy objective, for example, 120 years. Thereafter, deviation (negative) from expectation and course corrections are used to lower the life span objective to a life expectancy potential. The initial life expectancy potential of an individual will typically be based on parental genetic information and birth data. If no major change in health status has occurred, then the annual re-assessment of life expectancy potential will remain the same. If, however, major health events have taken place, then a re-assessment of life expectancy potential is to be made at that time (i.e., deviation from expectation). Major health events could involve the discovery of any chronic or acute disease, e.g., diabetes, cardiovascular disease, pulmonary disease, osteoporosis, obesity, etc. It can also include lifestyle changes and choices, such as, education, occupation, habits (e.g., smoking, alcohol consumption, exercise regime, etc.).

Figure 2:
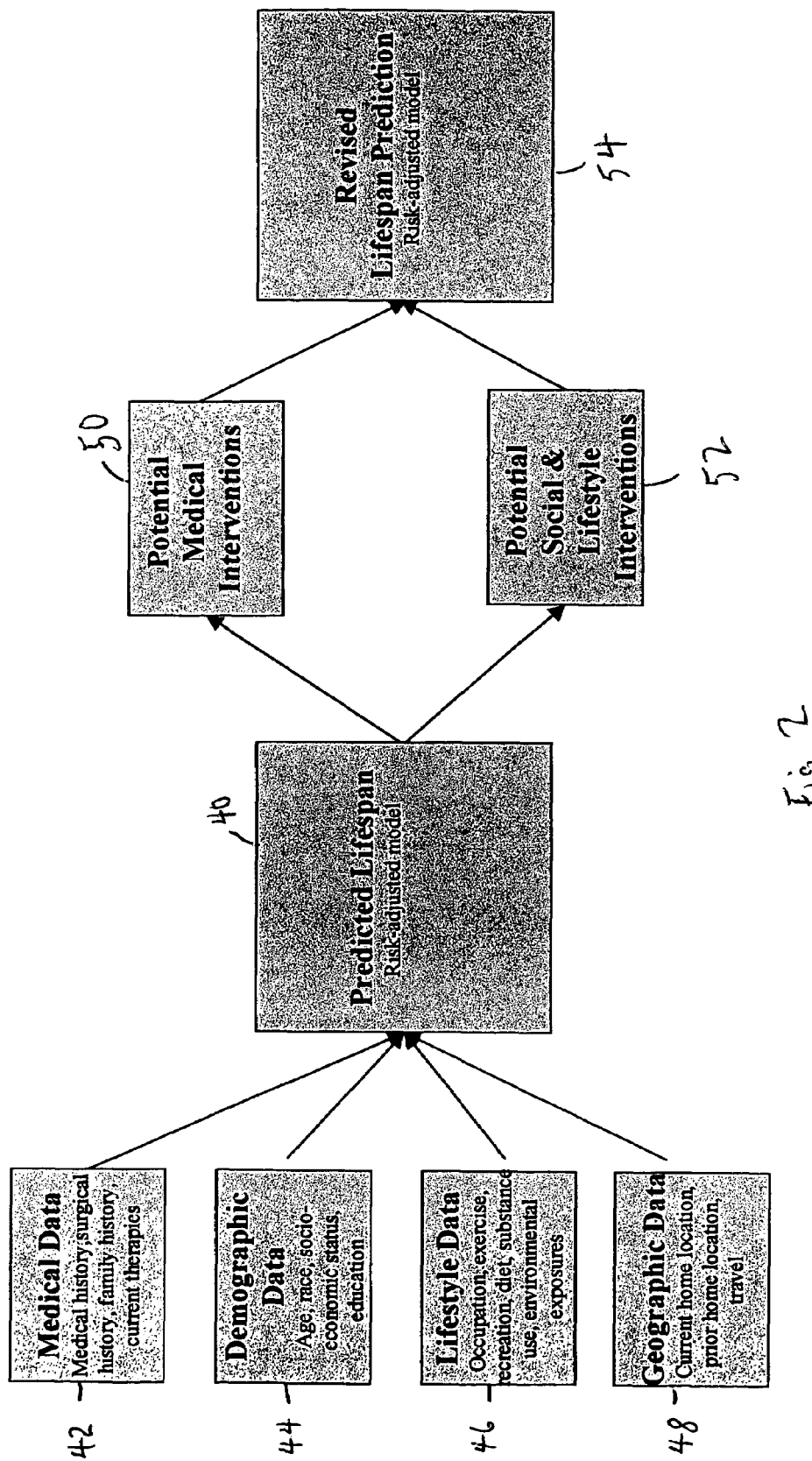
FIG. 2 is a schematic diagram of data used to revise a life expectancy potential according to one embodiment of the present invention.

One of the unique aspects of the present invention is that the life expectancy potential model can be used to counsel individuals by demonstrating how one's life expectancy potential can be increased or decreased by alternation in one's lifestyle, diet, and medication intake. For example, if an overweight smoker can be shown quantitatively that his or her life expectancy potential can be substantially increased by 10 or 20 years if the individual stops smoking, reduces his or her weight and begins to exercise, then it is quite possible that the individual will adjust his or her lifestyle in order to increase his or her life expectancy potential. This is best represented by the schematic diagram of FIG. 2, wherein a predicted lifespan or LED 40 is a risk adjusted model generated from medical data 42, demographic data 44, lifestyle data 46 and geographic data 48. Medical data 42 may include medical history, surgical history, family history and current therapies. Demographic data 44 includes age, race, socioeconomic status and education. Lifestyle data 46 includes occupation, exercise, recreation diet, substance use, and environmental exposures. Geographic data 48 includes current home location, prior home location and travel. Predicted lifespan 40 can then be revised via either potential medical interventions 50 and/or potential social and lifestyle interventions 52 in order to produce a revised lifespan prediction 54.

The modeling technique for the life expectancy potential and I.Q. is preferably imbedded or stored on a microprocessor which has the ability to predict within statistically significant limits, individual and specific life expectancy potential and I.Q. The microprocessor has the following characteristics: (a) capacity to receive all pertinent data concerning an individual; (b) ability to correlatively analyze the data and assign statistical importance to specific features; (c) ability to update itself based on evolving science; (d) ability to predict life expectancy potential and I.Q. within statistically significant limits; (e) ability to produce updated life expectancy potential and show the deviation (if any) for the projection; (f) in the event of a significant deviation from the projection, the microprocessor is able to analyze the deviation; (g) ability to show corrective measures to regain expected life expectancy potential; and (h) is programmed to produce a list of preventative measures to be taken in order to deal with potential and age-related problems, e.g., menopause, colonoscopy, prostate specific antigen, etc.

The microprocessor will initially be loaded with the following essential elements: (a) maternal and paternal genetic data; (b) ante-partum history and events, e.g., single/multiple gestation, maternal age, spontaneous or assisted pregnancy, chronic conditions, such as diabetes, hypertension and HIV/hepatitis infections, and other events, such as drug exposure; (c) birthing events, e.g., gestational age at delivery, type of delivery (e.g., normal/spontaneous, assisted, or cesarean), and apgar score at delivery; (d) neonatal history and events, e.g., biophysical profile, biochemical profile, uneventful neonatal course, and problem specific neonatal course (e.g., meconeum aspiration, infection, cerebral hemorrhage, etc.); and (e) socioeconomic factors, e.g., conventional family unit, single parent unit, ethnic background, etc.).

Each of the factors in the initial Modeling is assigned, based on statistical data, a percentage contribution to the life expectancy potential (LEP). That is, maternal and paternal genetics equal if, according to present day knowledge, both parents have a 'perfect' genetic background, then the percentage of the genetic contribution is hypothetically 80%, meaning that the genetic factor will be responsible for achieving 80% of the LEP, that being 120 years.

More specifically, assuming that maternal and paternal genetics contribute 80% to the overall LEP, then: (a) if the genetic factor is 'perfect', then there is a 0% deviation, meaning, based on genetic factors alone, that the individual should attain the age of 96; and (b) if there are other factors, such as, diabetes, renal disease, etc., then the genetic contribution to the LEP may drop to hypothetically 70%, meaning, based on genetic factors alone, that the individual should attain the age of 84.

All other factors will have an appropriate percent of input to the initial LEP determination. 120 years stands as the projection at today's state of the art of science of medicine and other factors. This number is also dynamic, based on the ever changing advances in medicine and socioeconomic conditions.

The I.Q. projections are also based on the above discussed factors and are to be developed accordingly. If all factors stated are ideal, then the percentage contribution from each factor is as initially stated. In the event that a specific factor becomes a critical factor (i.e., under 'Birthing Events', Baby Doe is delivered at an immature or premature stage of gestation, then this factor becomes the controlling factor in calculating LEP). The other factors will shift in their degree of importance in their contribution to the LEP and I.Q.

The modeling technique is to be universal, i.e., that all pertinent data on Baby Doe, when fed into the microprocessor, will produce and LEP and I.Q. that will be specific to Baby Doe with explanations, i.e., percentage deviations from the ideal (if any). Infancy data, adolescent data, and adult data, will be fed into the now specific model, at appropriate times, together with unexpected life events, i.e., surgeries, chronic diseases, etc.

There is a decremental life expectancy, i.e., each completed year of life will be subtracted from the initial LEP; if, however, there is an excessive deviation from the expected, then there is an explanation as to the cause by the updated model.

The explanation as to the cause of the deviation will serve as the basis for the interactive measures that can be taken by the individual to regain the projected LEP.

The individual's health profile data may also be used to track the census of a community. That is, an individual entering the community will deposit pertinent information into the community's information bank. This information can be used to update the communities ability to plan and project specific needs, e.g., healthcare planning, including specialized care, and educational needs (e.g., schools). Alternatively, selective information therefrom can be used to update the Center for Disease Control, as well as the National Census Bureau.

Figure 3:
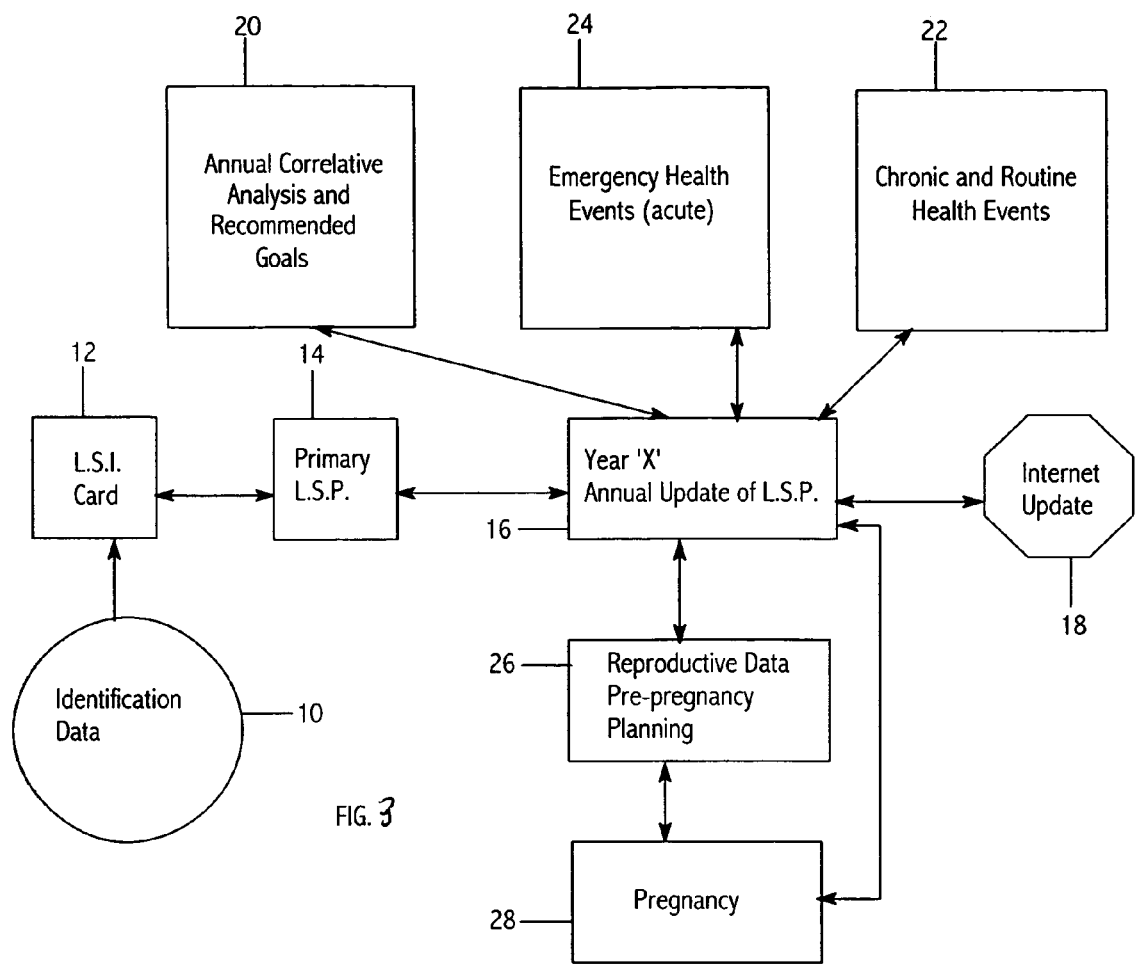
FIG. 3 is a block diagram depicting for establishing and updating medical information management card data.

FIG. 3 demonstrates the preferred health and life expectancy management system according to the present invention. Initially, identification data 10 is entered on a medical information management or life span interactive (LSI) card 12. The identification data may consist of primary identification data, such as, fingerprints, footprints, DNA and imagery of an individual, and secondary identification data, such as, insurance information, financial data, time elapse data and time at entry data. The identification data provides a level of security preventing basic entry to the information data by unauthorized individuals. Optionally, each card 12 would be equipped with an override key to be used by selected individuals, e.g., in case of an accident.

Subsequent to card 12 being loaded with identification data 10, primary life span projection (LSP) 14 is loaded onto card 12. Primary life span projection 14 is generated from at least one of the following pieces of data: maternal genetic data, paternal genetic data, socio-economic data, ante-partum data, birthing data and initial pediatric evaluation upon being discharged from the hospital. The primary life span projection 14 enables one to project the following: potential life span or expectancy, potential IQ, probability of contracting certain diseases, and probability of accidental death.

The life span potential prediction modeling logic according to the present invention is a dynamic modeling technique, meaning that it changes and adapts to developments/discoveries relating to health matters, e.g., new developments in diagnosis and treatment of specific diseases (including gene therapy), new developments in surgery (including organ replacements), and lifestyle changes including societal changes. This information is fed into the annual update of the life span potential 16 from specific sites on the Internet 18 which provides the most up to date information regarding specific disease and survival rate data pertaining thereto.

The prediction modeling logic base takes specific pertinent information regarding an individual's health information data and places it into an order of priorities and assigns percentages of importance to that specific event or data, e.g., (1) age, (2) gender, (3) health status, i.e., free of any chronic diseases or history of specific chronic diseases, (4) blood pressure, (5) weight, (6) habits, i.e., smoking, alcohol use, and specific sports, (7) social data, (8) environmental data such a type of work and conditions of one's work environment, and (9) educational status.

Based on the sub-total of the data, life span potential is then predicted. The predicted life expectancy is then correlated with the original projections and the deviation from the original is then analyzed. The analysis will result in a detailed report as to the (1) degree of deviation, (2) reasons for deviation, and (3) corrective measures that are necessary to regain the original life span potential predictions. The corrective measures are then presented to the individual and goals are set accordingly 20.

The basic recommendation to an individual concerning his or her health at the very least is the annual physical examination and the appropriate laboratory data 22. Also, emergency health events 24 also need to be included into the prediction modeling logic of annual update of life span potential 16. This new information will be used to create an updated prediction model. The new model will automatically be correlated with the previous model and an analysis 20 together with recommendations is generated. This analysis and recommendation 20 will be used by the healthcare professional in counseling the individual. If the new projections show negative deviations from the original life span or expectancy projections, then recommendations are made to repair the original objectives. Annual correlative analysis and recommended goals 20 can also be programmed to recommend preventive tests, such as, colonoscopy, mammography, and prostrate specific antigen (PSA).

Optionally, reproductive data for pre-pregnancy planning 26 or actual pregnancy 28 can be fed into prediction modeling logic 16 together with a potential partner's genetic data for the purpose of analyzing the composite data and identification of potential problems during the pregnancy. In the instance of possible infertility, the health profile data on card 12 can be used to follow the genetic line of the donor egg or sperm to insure against infertility. This data can also be used to advise couples of specific ante-partum (during the pregnancy) test to be considered, e.g., amniocentesis/chorionic villi sampling.

The prediction modeling logic 16 should also be updated during actual pregnancy with an initial assessment of the pregnant female, risk assignment, results of periodic reassessment according to preset schedule during the 40 week pregnancy, results of specific tests during the pregnancy, and updates to any changes of risk assignment, e.g., development of diabetes during pregnancy and development of elevated blood pressure. Other factors that may be fed to prediction modeling logic 16 are risk to mother, risk to baby, and type of delivery (e.g., spontaneous delivery, induction of labor and cesarean delivery).

Figure 4:
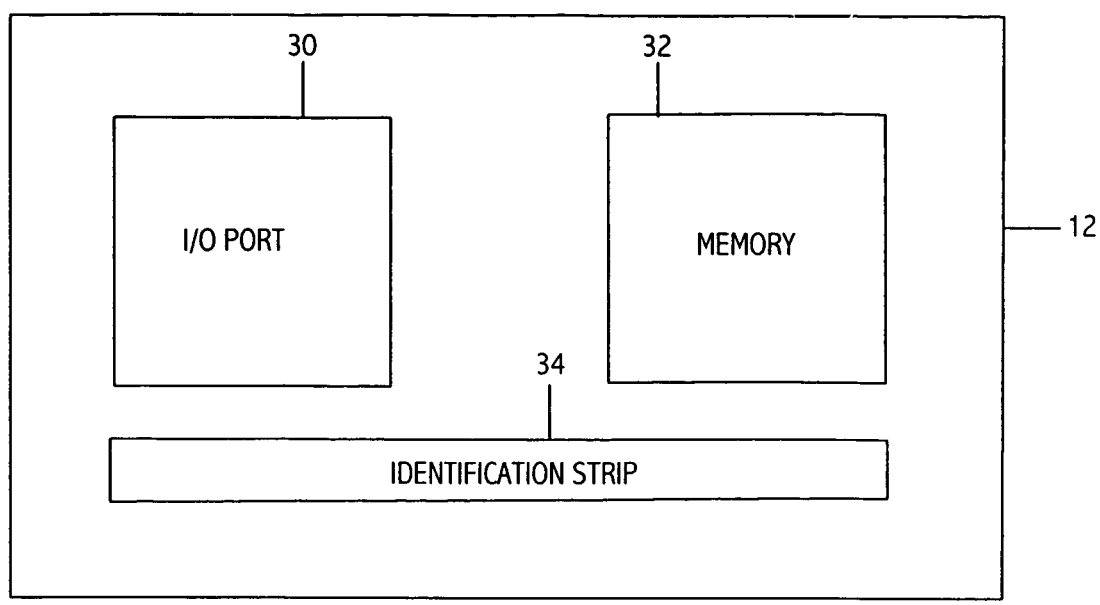
FIG. 4 is a block diagram of a medical information management card according to the present invention.

FIG. 4 depicts card 12 which typically includes an input/output port 30 to enable card 12 to interface with a computer which is capable of either uploading or downloading identification and health information data, a machine readable storage medium 32 which is capable of storing the identification and health information data, and an identification strip 34 which is capable of providing a security means to prevent unauthorized access to an individual's data.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A computer system for monitoring or managing life expectancy of a patient comprising:
    a computer memory storing (i) health profile data comprising medical history data describing said patient, and (ii) a patient-specific life expectancy potential (LEP) model determined in dependence on said patient's stored health profile data and comprising life expectancies for said patient and life expectancy importance factors assigned to specific health profile data elements; and
    at least one computer processor operatively coupled to said memory with prediction modeling logic for performing steps comprising:
        creating initially said patient-specific LEP model by correlative analysis of said patient's stored health profile data and a medical information bank, said medical information bank is at least one selected from the group consisting of: demographic, geographic, medical, and lifestyle information describing members of a population of a community of which said patient is a member;
        querying said patient-specific LEP model to determine a life expectancy for said patient should a selected future event occur in said patient's life; and
        updating said patient-specific LEP model upon addition of information to said patient's stored health profile data, to said information bank or to a combination thereof, said updating comprising further correlative analysis of said patient's stored health profile data and said information bank,
    wherein each of said life expectancy importance factors represents the percentage contribution to said life expectancy potential made by said specific health profile data element; and
    wherein each of said life expectancy importance factors is initially assigned a value based on statistical data, and wherein said value of each of said life expectancy importance factors changes according to the further correlative analysis of said patient's stored health profile data with said information bank.

2. The computer system of claim 1 wherein said patient medical history data is at least one selected from the group consisting of: birth data, pediatric data, adulthood health data, health data generated from said patient's visit to a healthcare provider, health data generated from medical therapy, health data generated from surgical treatment, and health data generated from psychiatric therapy.

3. The computer system of claim 1 wherein said information added to said patient's stored health profile data is at least one selected from the group consisting of: said patient's chronic or acute disease events, and said patient's lifestyle changes and choices.

4. The computer system of claim 1 wherein said information added to said patient's stored health profile data is at least one selected from the group consisting of: developments or discoveries relating to health matters, and medical information describing new members of said community.

5. The computer system of claim 1 wherein said computer processor comprises a microprocessor.

6. The computer system of claim 1 wherein said future event is at least one selected from the group consisting of: changes in said patient's lifestyle, changes in said patient's diet, and changes in said patient's medication intake.

7. The computer system of claim 1 further comprising means for providing secure access only to said health profile data.

8. A portable electronic device for monitoring or managing life expectancy of a patient comprising:
    a computer memory having encoded therein:
        health profile data comprising medical history data describing said patient, and
        a patient-specific life expectancy potential (LEP) model determined in dependence on said patient's stored health profile and comprising life expectancies for said patient and life expectancy importance factors assigned to specific health profile data elements, said LEP model being created initially by correlative analysis of said patient's stored health profile data and a medical information bank, said medical information bank is at least one selected from the group consisting of: demographic, geographic, medical, and lifestyle information describing members of a population of a community of which said patient is a member; and
    an I/O interface permitting external access to said computer memory for:
        querying said specific LEP model to determine expected effects on said patient of a proposed or actual alteration and events in said patient's life; and
        updating said specific LEP model upon addition of information to said patient's stored health profile data and/or to said information bank, said updating comprising further correlative analysis of said patient's stored health profile data and said information bank,
    wherein each of said life expectancy importance factors represents the percentage contribution to said life expectancy potential made by said specific health profile data element: and
    wherein each of said life expectancy importance factors is initially assigned a value based on statistical data and wherein said value of each of said life expectancy importance factors chances according to the further correlative analysis of said patient's stored health profile data with said information bank.

9. The portable electronic device of claim 8 wherein said computer memory further encodes access control data.

10. The portable electronic device of claim 9 wherein said access control data is at least one selected from the group consisting of: fingerprint identification data, footprint identification data, DNA identification data, imagery identification data, and password data.

11. The portable electronic device of claim 8 wherein said information added to said patient's stored health profile data is at least one selected from the group consisting of: developments or discoveries relating to health matters, and medical information describing new members of said community.

12. A method for monitoring or managing life expectancy of a patient comprising:
   creating initially a patient-specific life expectancy potential (LEP) model by correlative analysis of said patient's stored health profile data and a medical information bank, said medical information bank is at least one selected from the group consisting of: demographic, geographic, medical, and lifestyle information describing members of a population of a community of which said patient is a member, said patient-specific LEP model determined in dependence on said patient's stored health profile describing life expectancies for said patient and life expectancy importance factors assigned to specific health profile data elements, and said creating comprising computer execution of a plurality of computer instructions;
   querying said patient-specific LEP model to determine a life expectancy for said patient should a selected future event occur in said patient's life, and said querying comprising computer execution of a plurality of computer instructions; and
   updating said patient-specific LEP model upon addition of information to said patient's stored health profile data and/or to said information bank, said updating comprising computer execution of a plurality of computer instructions that perform further correlative analysis of said patient's stored health profile data and said information bank,
   wherein each of said life expectancy importance factors represents the percentage contribution to said life expectancy potential made by said specific health profile data element; and
   wherein each of said life expectancy importance factors is initially assigned a value based on statistical data and wherein said value of each of said life expectancy importance factors changes according to the further correlative analysis of said patient's stored health profile data with said information bank.

13. The method of claim 12 wherein said future event is at least one selected from the group consisting of: changes in said patient's lifestyle, changes in said patient's diet, and changes in said patient's medication intake.

14. The method of claim 12 wherein said LEP model comprises an initial life expectancy potential determination and one or more life expectancy importance factors assigned to specific health profile data elements, and wherein said correlative analysis comprises dynamically deriving said importance factors from correlation of said patient's stored health profile data to said information bank.

15. The method of claim 14 wherein said querying said LEP model comprises reducing said initial life expectancy potential determination by amounts dependent on said life expectancy importance factors assigned to said future event.

16. The method of claim 12 further comprising:
   querying said patient-specific LEP model to determined expected alternative life expectancies in case of selected changes in said patient's lifestyle, on changes in said patient's diet, changes in said patient's medication intake, or any combination thereof; and
   recommending to said patient suitable changes in lifestyle, diet, medication intake or any combination thereof that advantageously effect said patient's expected life expectancy.

17. The method of claim 16 further comprising querying said patient-specific LEP model to determine an expected life expectancy of said patient in the absence of future changes.

18. The method of claim 17 wherein an advantageous effect on said patient's expected life expectancy comprises an expected life expectancy greater than said expected life expectancy in the absence of future changes.

19. The method of claim 12 further comprising the step depositing the health profile data of a new member of said community in said information bank.

20. A computer memory comprising encoded instructions for causing a computer processor to:
   create initially a patient-specific life expectancy potential (LEP) model by correlative analysis of said patient's stored health profile data and a medical information bank, said medical information bank is at least one selected from the group consisting of: demographic, geographic, medical, and lifestyle information describing members of a population of a community of which said patient is a member, said patient-specific LEP model determined in dependence on said patient's stored health profile describing life expectancies for said patient and life expectancy importance factors assigned to specific health profile data elements, and said creating comprising computer execution of a plurality of computer instructions;
   query said patient-specific LEP model to determine a life expectancy for said patient should a selected future event occur in said patient's life; and
   update said specific LEP model upon addition of information to said patient's stored health profile data and/or to said information bank, said updating comprising further correlative analysis of said patient's stored health profile data and said information bank,
   wherein each of said life expectancy importance factors represents the percentage contribution to said life expectancy potential made by said specific health profile data element; and
   wherein each of said life expectancy importance factors is initially assigned a value based on statistical data, and wherein said value of each of said life expectancy importance factors changes according to the further correlative analysis of said patient's stored health profile data with said information bank.

21. The computer memory of claim 20 further comprising encoded information describing the following:
   health profile data comprising medical history data of said patient, and
   a patient-specific life expectancy potential (LEP) model comprising life expectancies now expected for said patient after taking account of the events described in said patient's stored health profile, said LEP model being created initially by correlative analysis of said patient's stored health profile data and a medical information bank, said medical information bank is at least one selected from the group consisting of: demographic, geographic, medical, and lifestyle information describing members of a population of a community of which said patient is a member.

22. The computer system of claim 1, wherein said memory further comprises:
   encoded information describing an I/O interface permitting external access to said computer memory for querying said patient-specific LEP model to determine expected effects on said patient of a proposed or actual alteration and events in said patient's life; and updating said patient-specific LEP model upon addition of information to said patient's stored health profile data and/or to said information bank, said updating comprising further correlative analysis of said patient's stored health profile data and said information bank.

* * * * *